United States Patent [19]

Stevenson et al.

[11] Patent Number: 5,849,821

[45] Date of Patent: Dec. 15, 1998

[54] TRIS-ARYL-S-TRIAZINES SUBSTITUTED WITH BIPHENYLYL GROUPS

[75] Inventors: Tyler A. Stevenson, Teaneck, N.J.;
Revathi Iyengar, Cortland Manor;
Ramanathan Ravichandran, Nanuet, both of N.Y.

[73] Assignee: Ciba Specialty Chemicals Corporation, Tarrytown, N.Y.

[21] Appl. No.: 925,016

[22] Filed: Sep. 8, 1997

Related U.S. Application Data

[62] Division of Ser. No. 703,751, Aug. 27, 1996, Pat. No. 5,726,309.

[51] Int. Cl.⁶ .......................... C08K 5/3492; B32B 15/04
[52] U.S. Cl. .......................... 524/100; 428/457; 428/463; 524/99; 524/91; 524/222; 524/344
[58] Field of Search .......................... 524/100; 428/457, 428/463

[56] References Cited

U.S. PATENT DOCUMENTS

| | | | |
|---|---|---|---|
| 3,118,887 | 1/1964 | Hardy et al. | 260/248 |
| 3,242,175 | 3/1966 | Duennonberger et al. | 260/248 |
| 3,244,708 | 4/1966 | Duennonberger et al. | 260/248 |
| 3,268,474 | 8/1966 | Hardy et al. | 260/458 |
| 3,444,164 | 5/1969 | Luethi et al. | 260/248 |
| 4,619,956 | 10/1986 | Susi | 524/87 |
| 4,740,542 | 4/1988 | Susi | 524/87 |
| 4,826,978 | 5/1989 | Migdal et al. | 524/100 |
| 4,831,068 | 5/1989 | Reinert et al. | 524/100 |
| 4,950,304 | 8/1990 | Reinert et al. | 8/566 |
| 4,962,142 | 10/1990 | Migdal et al. | 524/100 |
| 5,096,489 | 3/1992 | Laver | 106/20 |
| 5,106,891 | 4/1992 | Valet | 524/91 |
| 5,288,778 | 2/1994 | Schmitter et al. | 524/100 |
| 5,298,067 | 3/1994 | Valet et al. | 106/506 |
| 5,354,794 | 10/1994 | Stevenson et al. | 524/100 |
| 5,461,151 | 10/1995 | Waterman | 544/216 |
| 5,726,309 | 3/1998 | Stevenson et al. | 544/216 |

FOREIGN PATENT DOCUMENTS

| | | |
|---|---|---|
| 0165608 | 12/1985 | European Pat. Off. |
| 0442847 | 4/1990 | European Pat. Off. |
| 0434608 | 6/1991 | European Pat. Off. |
| 0444323 | 9/1991 | European Pat. Off. |
| 0468921 | 1/1992 | European Pat. Off. |
| 0483488 | 5/1992 | European Pat. Off. |
| 0704437 | 4/1996 | European Pat. Off. |
| 9628431 | 9/1996 | WIPO. |

OTHER PUBLICATIONS

Chemical Abstract 72:90534n, vol. 72, 1970 p. 411.

*Primary Examiner*—Mukund J. Shah
*Assistant Examiner*—Pavanaram K. Sripada
*Attorney, Agent, or Firm*—Luther A. R. Hall

[57] ABSTRACT

Selected s-triazines of formula I

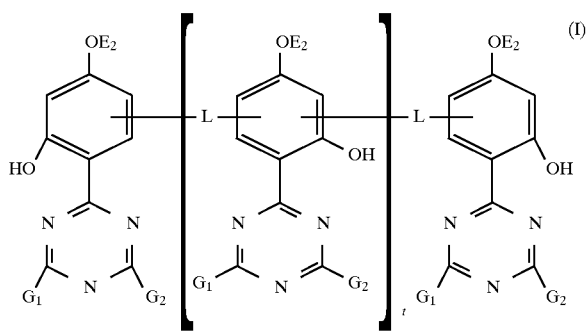

where $G_1$ and $G_2$ are biphenylyl moieties, are UV absorbers having high thermal stability and surprisingly high extinction coefficients making them of especial interest in stabilizing automotive coatings where such properties are highly valued.

21 Claims, No Drawings

TRIS-ARYL-S-TRIAZINES SUBSTITUTED WITH BIPHENYLYL GROUPS

This is a divisional of application Ser. No. 08/703,751, filed on Aug. 27, 1996, which is now U.S. Pat. No. 5,726,309, issued on Mar. 10, 1998.

The s-triazines of formula I are UV absorbers having high thermal stability and surprisingly high extinction coefficients making them of especial value for stabilizing polymer substrates, especially automotive coatings.

Tris-aryl-s-triazines in which at least one of the aryl groups has an hydroxy group ortho to the point of attachment to the triazine ring are well known UV absorbers. It is also well-known that this class of triazines protect organic polymers from the deleterious effects of exposure to actinic radiation.

For the purposes of this application 2,4-dihydroxyphenyl groups on a s-triazine ring may be referred to as resorcinol groups. The numbering system used on the resorcinol group is outlined as follows:

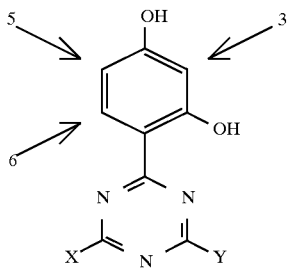

U.S. Pat. Nos. 3,118,887 and 3,268,474 describe the protection of plastic and resinous compositions from UV light by the incorporation of one or more compounds with the class of tris-aryl-s-triazines. The former patent claims 2,4,6-tris-(2,4-dihydroxyphenyl)-s-triazine and 2,4,6-tris-(2-hydroxy-4-alkoxyphenyl)-s-triazines. A tris-5-alkylresorcinol-s-triazine is prepared, but not tested or claimed.

U.S. Pat. No. 3,268,474 claims the composition of a polymeric material and a tris-aryl-s-triazine that has at least one ortho-hydroxyphenyl group and which may be further substituted on each of the three aryl rings by alkyl, alkoxy, halo, etc., with a total of up to three substituents on each ring. Preferred substitution patterns are not given. There are specific claims for compositions including tris-(2-hydroxy-4-alkoxyphenyl)-s-triazines and 2,4-bis-(2,4-dimethylphenyl)-6-(2-hydroxy-4-octyloxyphenyl)-s-triazine. Again, an example of a tris-alkylresorcinol-s-triazine is given, but it is not tested and its composition with a polymer is not claimed.

U.S. Pat. No. 3,242,175 claims bis-resorcinol-tris-aryl-s-triazines with no substitution on the resorcinol rings. U.S. Pat. No. 3,244,708 claims mono-, bis-, or tris-resorcinol-tris-aryl-s-triazines with no substitution on the resorcinol rings. A Markush structure in the introduction of the patent does refer to mono-resorcinol-tris-aryl-s-triazines that may be further substituted on the resorcinol ring by one or two or combinations of hydroxy, halogen, alkyl, alkoxy, phenyl, or phenylalkyl. Preferred substitution patterns are not mentioned and no such compounds are synthesized or tested.

U.S. Pat. Nos. 4,619,956 and 4,740,542 disclose the use of synergistic amounts of tris-aryl-s-triazines and hindered amine light stabilizers in polymer film coatings or molded articles against the action of light, moisture and oxygen. The tris-aryl-s-triazines referred to in these patents are those described in U.S. Pat. No. 3,268,474. The preferred s-triazine is 4,6-bis-(2,4-dimethylphenyl)-2-(2,4-dihydroxyphenyl)-s-triazine or 4,6-bis-(2,4-dimethylphenyl)-2-(2-hydroxy-4-octyloxyphenyl)-s-triazine. A Markush structure in the patents describes tris-aryl-s-triazines with at least one hydroxy group ortho to the point of attachment to the triazine ring and which may have up to three substituents on each of the three aryl rings. These substituents include alkyl, alkoxy, halo, etc. Preferred substitution patterns are not given and no compounds with substitution on a resorcinol ring are prepared or tested. Additionally, while these two patents generically describe mono-s-triazines substituted inter alia with biphenylyl groups, no specific mono-s-triazine having biphenylyl groups are disclosed and the beneficial high extinction coefficients afforded by such groups not disclosed as well.

E.P. Application No. 444,323 claims highly-soluble tris-aryl-s-triazines, the process for their preparation, and their composition with an organic solvent. A specific triazine mentioned as useful in this process is 2-(2,4-dihydroxyphenyl)-4,6-bis-(2,4-dimethylphenyl)-s-triazine. The tris-aryl-s-triazines claimed in this application are based on those described in U.S. Pat. 3,268,474. The preferred triazines are mono-resorcinol-tris-aryl based s-triazines. The preferred Markush group shows that the resorcinol ring may be further substituted in the 5-position with alkyl groups. However, the effects of substitution in this position are not mentioned, and no such compounds are prepared or tested.

E.P. Application No. 483,488 and U.S. Pat. No. 5,461,151 claims the synergistic stabilizer composition comprised of a tris-aryl-s-triazine and a hindered amine and the method of stabilizing a polymer by incorporating such a composition. Again, the triazines claimed in the compositions are based on those described in U.S. Pat. 3,268,474. The preferred triazines are bis-xylyl-resorcinol based s-triazines. The body of the application does show a Markush structure of a mono-resorcinol-tris-aryl based s-triazine that may be further substituted in the 5-position of the resorcinol ring with alkyl groups. However, no triazines with such further substitution on the resorcinol ring are prepared or tested.

U.S. Pat. Nos. 4,826,978 and 4,962,142 disclose a class of tris-aryl-s-triazines useful as ultraviolet screens for polymers, including coatings. The triazines are based on bis-resorcinol-phenyl-s-triazines with electron withdrawing groups substituted on the phenyl group. No further substitution on the resorcinol groups are referred to.

U.S. Pat. No. 5,106,891 claims coating compositions which contain, as the UV absorber, a mixture of at least one 2-hydroxyphenylbenzotriazole and at least one 2-hydroxyphenyltriazine. The triazines described are based on mono-resorcinol-tris-aryl-s-triazines, with the preferred structure based on bis-xylyl-resorcinol-s-triazine. The Markush structure discloses that the aryl groups may be substituted by up to three hydroxyl, halogenomethyl, alkyl, alkoxy or halogen, or combinations thereof. Structures are disclosed, therefore, of tris-aryl-s-triazines with substituted resorcinol groups, but preferred substitution patterns are not disclosed, and no such compounds are prepared or tested.

E.P. Application No. 434,608 claims an organic material which has been stabilized against damage by light, heat and oxygen and which contains a combination of a hindered amine and an o-hydroxyphenyl-s-triazine or said triazine alone, the process for stabilizing an organic material by incorporation of the combination of a hindered amine and said triazine or triazine alone, novel o-hydroxyphenyl-s-triazines, and the use of novel s-triazines as a stabilizer for organic materials. Organic materials specifically mentioned are coating binders and radiation-curable coating materials. The preferred triazines are mono-resorcinol-tris-aryl based s-triazines with no further substitution on the resorcinol ring. A Markush structure is claimed that covers tris-aryl-s-triazines with one or two alkyl- or halo-substituted resorcinol groups. Preferred substitution patterns are not given, and no compounds with substituted resorcinol rings are prepared or tested.

E.P. Application No. 442,847 claims a coating composition that contains a binder, a hardening agent, and a tris-aryl-s-triazine as a stabilizer against damage by light, heat, and oxygen. Specifically mentioned is the use of this composition for automobile coatings. Preferred triazines for use in this composition are mono-resorcinol-tris-aryl based s-triazines with no substitution on the resorcinol ring. A Markush structure is described in the claim section that includes tris-aryl-s-triazines with one or two resorcinol groups that may be further substituted by alkyl or halogen. Preferred substitution patterns are not given, and no compounds with substituted resorcinol rings are prepared or tested.

U.S. Pat. No. 5,354,794 claims a polymer film composition which comprises an electro coat primer, a color coat in adhesion to the electro coat, a clear coat in adhesion to the color coat, and a tris-aryl-s-triazine UV absorber in either the color coat or clear coat or both. It is pointed out that a particular subgenus of tris-aryl-s-triazines, those based on bis- and tris-resorcinol-tris-aryl-s-triazines are especially effective in stabilizing such a coating system. A Markush structure in the composition claims describes bis- and tris-resorcinol-tris-aryl-s-triazines that may be substituted on the resorcinol rings by an alkyl of 1 to 6 carbon atoms. Specific substitution patterns are not discussed. An example of the preparation of 2,4,6-tris-(2,4-dihydroxy-5-hexylphenyl)-s-triazine is given, but this compound is not tested.

U.S. Pat. No. 5,298,067 claims a coating material stabilized with monomers or dimers of mono-resorcinol-tris-aryl based s-triazines alone or in combination with a hindered amine or an hydroxyphenylbenzotriazole, and the method of stabilizing a coating material by incorporating these s-triazines. No further substitution on the resorcinol groups is referred to. A coating material specifically mentioned is an automotive lacquer.

E.P. Application No. 165,608 discloses s-triazines including a class of tris-aryl-s-triazines, the process for their preparation, and their method of use as UV absorbers in organic materials, especially color photographic materials. Tris-aryl-s-triazines disclosed include those with one to three resorcinol groups that may be substituted with alkyl, alkoxy, hydroxy, or alkyl or phenylcarbonyl. Preferred substitution patterns are not disclosed. Examples are given for bis-resorcinol-tris-aryl-s-triazines with the resorcinol substituted in the 3-position by methyl, in the 6position by hydroxy, methoxy, and methyl, and in the 5-position by acetyl.

U.S. Pat. No. 3,843,371 claims photographic material which contains a tris-aryl-s-triazine as a stabilizer against UV radiation. A Markush structure in the claims of this patent includes bis-resorcinol-tris-aryl-s-triazines that may have an alkyl substituent in the 6position of one of the resorcinol rings. Preferred triazines are bis-resorcinol-tris-aryl based s-triazines with no further substitution on the resorcinol rings. A Markush structure in the body of the patent describes tris-aryl-s-triazines that may have one or two resorcinol groups that may be substituted with halogen, hydroxyl, alkyl, alkoxy, phenyl, phenoxy, cycloalkoxy, etc. Preferred substitution patterns are not discussed and no compounds with substituted resorcinol groups are prepared or tested.

E.P. Application No. 468,921 claims aqueous dispersions of s-triazines with at least one anionic or non-ionic compound. The Markush structure in the claim section includes tris-aryl-s-triazines possibly having one resorcinol ring substituted by alkyl or halogen. The substitution pattern is not specified. The preferred triazines include mono-resorcinol-tris-aryl based s-triazines with no substitution on the resorcinol ring and are the only s-triazines exemplified. U.S. Pat. No. 4,831,068 claims a process for stabilizing dyeings on polyester fiber materials with a s-triazine UV absorber and the polyester fiber material treated by such a process. The Markush structure and preferred triazines are the same as in E.P. Application No. 468,921. Again, only s-triazines of the preferred type are shown in the examples.

U.S. Pat. No. 4,950,304 claims the process of quenching or suppressing the fluorescence of natural or synthetic polyamide substrates treated with whitening agents. The process comprises applying to said substrates a liquor containing an hydroxyphenylbenzotriazole or an hydroxyphenyltriazine and fixing said UV absorber thereon. The Markush structure of s-triazines disclosed includes tris-aryl-s-triazines that may have a substituted resorcinol group. The resorcinol group may be substituted in the 3- or 5-position by halogen, alkyl, cycloalkyl, phenylalkyl, sulfo, etc. Preferred triazine structures are bis-phenyl-resorcinol-s-triazines with a sulfonate group substituted in the 5-position of the resorcinol ring. No s-triazines with resorcinol groups substituted with any of the other substituents are prepared or tested. The advantage of substitution in the 5-position over the 3-position of resorcinol is not discussed.

U.S. Pat. No. 5,096,489 claims a method of stabilizing an ink jet print with the use of an aqueous solution of a dye in combination with a s-triazine. A Markush structure describes tris-aryl-s-triazines that may have one or more resorcinol groups substituted in the 5-position by a sulfo, halo, or alkyl group. The preferred triazines for use in this method are based on bis- and tris-resorcinol-tris-aryl-s-triazines with no substitution on the resorcinol rings. No s-triazines with substituted resorcinol groups are exemplified. Advantages of substitution in the 5-position of the resorcinol ring are not discussed.

None of the above references specifically disclose s-triazines substituted with biphenylyl groups and none of the references disclose the beneficial high extinction coefficients afforded by such groups.

Copending application Ser. No. 08/281,381 discloses dimeric and lower oligomeric substituted s-triazine UV absorbers, but not said s-triazines substituted by biphenylyl groups.

DETAILED DISCLOSURE OF THE INVENTION

The instant invention pertains to novel dimeric or oligomeric tris-aryl-s-triazines wherein at least one of the aryl groups is a biphenylyl or substituted biphenylyl moiety.

More particularly, the instant invention relates to compounds of formula I

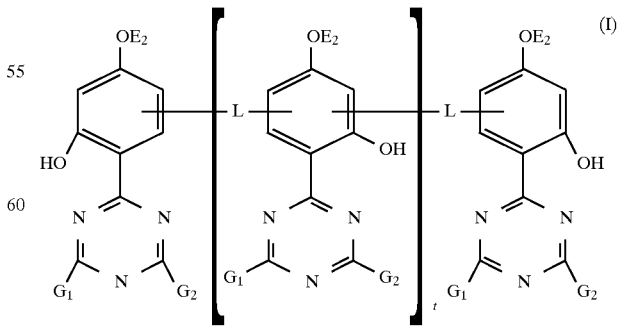

wherein $G_1$ is a group of the formula

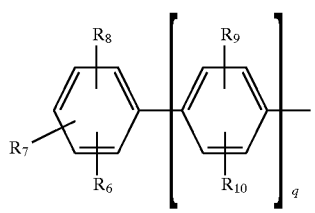

$G_2$ is a group of the formula

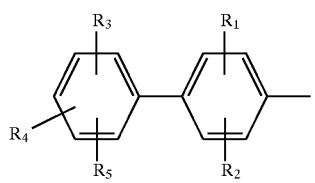

where q is 0 or 1, $R_1$, $R_2$, $R_3$, $R_4$, $R_5$, $R_6$, $R_7$, $R_8$, $R_9$ and $R_{10}$ are independently of one another hydrogen, hydroxyl, cyano, alkyl of 1 to 20 carbon atoms, alkoxy of 1 to 20 carbon atoms, phenylalkyl of 7 to 15 carbon atoms, cycloalkyl of 4 to 12 carbon atoms, cycloalkoxy of 4 to 12 carbon atoms, halogen, haloalkyl of one to 5 carbon atoms, sulfonyl, carboxyl, acylamino of 2 to 12 carbon atoms, acyloxy of 2 to 12 carbon atoms, alkoxycarbonyl of 2 to 12 carbon atoms, aminocarbonyl, or $R_3$ and $R_4$ together with the phenyl radical to which they are attached, are a cyclic radical interrupted by one or more oxygen or nitrogen atoms, $E_2$ is hydrogen, straight or branched chain alkyl of 1 to 24 carbon atoms or cycloalkyl of 5 to 12 carbon atoms; or said alkyl or cycloalkyl substituted by one to eight halogen, epoxy, glycidyloxy, furyloxy, —$E_4$, —$OE_5$, —$N(E_5)_2$, —$CON(E_5)_2$, —$COE_5$, —$COOE_5$, —$OCOE_5$, —$OCOC(E_5)=C(E_5)_2$, —$C(E_5)=CCOOE_5$, —CN, —NCO, or

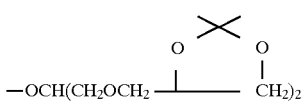

combinations thereof; or said alkyl or cycloalkyl interrupted by one to six epoxy, —O—, —$NE_5$—, —$CONE_5$—, —COO—, —OCO—, —CO—, —$C(E_5)=C(E_5)COO$—, —$OCOC(E_5)=C(E_5)$—, —$(E_5)C=C(E_5)$—, phenylene, or -phenylene-$G_3$-phenylene in which $G_3$ is —O—, —S—, —$SO_2$—, —$CH_2$—, or —$C(CH_3)_2$—, or combinations thereof; or said alkyl or cycloalkyl both substituted and interrupted by combinations of the groups mentioned above; or $E_2$ is —$SO_2E_3$, or —$COE_6$;

$E_4$ is aryl of 6 to 10 carbon atoms, or said aryl substituted by one to three halogen, alkyl of 1 to 8 carbon atoms, alkoxy of 1 to 8 carbon atoms or combinations thereof; cycloalkyl of 5 to 12 carbon atoms; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; or straight or branched chain alkenyl of 2 to 18 carbon atoms;

$E_5$ is defined as $E_4$, or $E_5$ is also hydrogen or straight or branched chain alkyl of 1 to 24 carbon atoms; or $E_5$ is a group of the formula

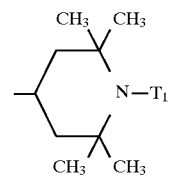

where $T_1$ is hydrogen, oxyl, hydroxyl, alkyl of 1 to 12 carbon atoms, said alkyl substituted by at least one hydroxyl or lower alkoxy, benzyl or alkanoyl of 2 to 18 carbon atoms;

$E_6$ is straight or branched chain alkyl of 1 to 18 carbon atoms, straight or branched chain alkenyl of 2 to 18 carbon atoms, phenyl, alkoxy of 1 to 12 carbon atoms, phenoxy, alkylamino of 1 to 12 carbon atoms, arylamino of 6 to 12 carbon atoms or a group —$E_7$COOH or —NH—$E_8$—NCO;

$E_7$ is alkylene of 2 to 14 carbon atoms or o-phenylene;

$E_8$ is alkylene of 2 to 10 carbon atoms, phenylene, tolylene, diphenylenemethane or a group

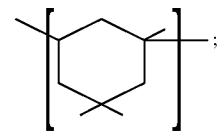

t is 0 to 9; and

L is straight or branched chain alkylene of 1 to 12 carbon atoms, cycloalkylene of 5 to 12 carbon atoms, alkylene substituted by or interrupted by cyclohexylene or phenylene; or L is benzylidene; or L is —S—, —S—S—, —S—$L_1$—S—, —SO—, —$SO_2$—, —SO—$L_1$—SO—, —$SO_2$—$L_1$—$SO_2$—, —$CH_2$—NH—$L_1$—NH—$CH_2$— or $$-\underset{\underset{CH_3}{|}}{\overset{\overset{CH_3}{|}}{C}}-\underset{}{\overset{}{\bigcirc}}\hspace{-2pt}\diagdown CH_3$$

where $L_1$ is alkylene of 2 to 12 carbon atoms, cycloalkylene of 5 to 12 carbon atoms, or alkylene interrupted or terminated by cyclohexylene of 8 to 12 carbon atoms; with the proviso that at least one L linkage is attached to the phenyl ring in the 5-position.

Preferably, t is 0 to 3, most preferably 0 indicating a dimeric structure. In addition to discrete dimers substituted on both resorcinol moieties in the 5-positions, it is possible under selected conditions to synthesize a "dimer mixture" as well as higher oligomers where the resorcinol derived rings are bound through both the 5 and 3 positions. The 5:5 and 5:3 substituted dimers are the major components of these mixtures. Because there is a large proportion of 5-substituted resorcinol rings these mixtures are red-shifted. The isomers can be separated by chromatographic or other organic chemistry separation techniques, but the mixture itself is red-shifted and can be used as is as an effective UV absorber stabilizer. In addition to being red-shifted, the isomer mixture is very highly soluble in common organic solvents.

Preferably, $G_1$ and $G_2$ are biphenylyl or biphenylyl substituted with one to three lower alkyl or halogen;

$E_2$ is straight or branched chain alkyl of 2 to 24 carbon atoms, or said alkyl substituted by one or two —$OE_5$, where $E_5$ is hydrogen, straight or branched chain alkyl of 1 to 24 carbon atoms, or phenyl.

Most preferably, $E_2$ is alkyl of 2 to 24 carbon atoms substituted by one hydroxyl and by one —$OE_5$ where $E_5$ is alkyl of 1 to 24 carbon atoms or phenyl.

Still other preferred embodiments of the invention are to a compound of formula I where $G_1$ and $G_2$ are biphenylyl or biphenylyl substituted with one to three lower alkyl or halogen;

t is 0 to 3; and

L is methylene; benzylidene;

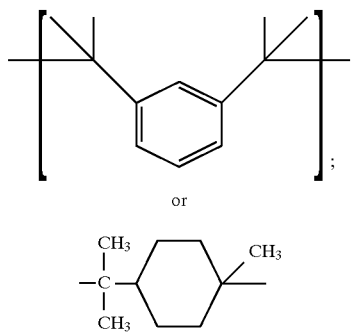

or

Especially preferred are the compound of formula I where $G_1$ and $G_2$ are 4-biphenylyl;

$E_2$ is straight or branched chain alkyl of 2 to 6 carbon atoms, or said alkyl substituted by one or two —$OE_5$ where $E_5$ is hydrogen or straight or branched chain alkyl of 1 to 24 carbon atoms.

Another preferred embodiment is a compound of formula I wherein $E_2$ is alkyl of 1 to 24 carbon atoms substituted by one hydroxyl and by one alkoxy of 1 to 24 carbon atoms.

Preferred compounds of formula I are:

a. 1,3-bis{1-[2,4-dihydroxy-5-(3,5-di(4-biphenylyl)-s-triazinyl))phenyl]-1-methyl-ethyl}benzene;

b. mixture of methylene-bis-[2-(2-hydroxy-4-octyloxyphenyl)-4,6di(4-biphenylyl)-s-triazine bridged]in the 3:5, 5:5 and 3:3 positions in a 5:4:1 ratio; and c. mixture of benzylidene-bis-[2-(2-hydroxy-4-octyloxyphenyl)-4,6-di-(4-biphenylyl)-s-triazine]; bridged in the 3:5 and 5:5 positions in a 1:1 ratio.

When any of the groups designated in the formulas is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl and n-octadecyl; when alkylene, such alkylene groups are, for example, ethylene, trimethylene, tetramethylene, hexamethylene, octamethylene and 2,2-dimethylpropane-1,3-diyl; when cycloalkylene, such cycloalkylene groups are, for example, cyclopentylene or cyclohexylene; when phenyl substituted by alkyl or alkoxy, such groups are, for example, tolyl, xylyl or methoxyphenyl; when cycloalkyl, such groups are, for example, cyclopentyl, cyclohexyl, cyclooctyl or cyclododecyl; when phenylalkyl, such groups are, for example, benzyl, α-phenethyl, 2-phenethyl or 4-tert-butylbenzyl; when alkyl which are interrupted by —O— or —$NR_5$— and can be substituted by OH are, for example, methoxyethyl, ethoxyethyl, butoxyethyl, butoxypropyl, $CH_3OCH_2CH_2OCH_2CH_2$—, $CH_3CH_2OCH_2CH_2OCH_2CH_2$—, $C_4H_9OCH_2CH_2OCH_2CH_2$—, dodecyloxypropyl, 2-hydroxyethyl, 2-hydroxypropyl, 4-hydroxybutyl, 6hydroxyhexyl, —$CH_2CH_2$—$NH$—$C_4H_9$, —$CH_2CH_2CH_2NH$—$C_8H_{17}$, —$CH_2CH_2CH_2$—$N(CH_3)$—$CH_2CH(C_2H_5)C_4H_9$, 2-hydroxy-3-nonyloxypropoxy and 2-hydroxy-3-dodecyloxypropoxy.

Another feature of this invention are the processes by which these products may be obtained. The construction of the tris-aryl-s-triazine nucleus is well known and is described in U.S. Pat. Nos. 3,268,474 and 3,244,708. What is claimed here are the processes by which a resorcinol group of a tris-aryl-s-triazine may be "post-alkylated," that is, functionalized by substitution in the 5-position with a saturated carbon.

The intermediates and reagents required to make the instant compounds are largely items of commerce or can be obtained by methods known in the art.

Numerous processes may be employed for this "alkylation". Friedel-Crafts alkylations with alkenes, alkyl halides or alcohols using the appropriate catalyst, e.g. aluminum chloride, p-toluenesulfonic acid, methanesulfonic acid, etc.; reduction of the product of a Friedel-Crafts acylation; metal-phenoxide additions across activated (Michael) or unactivated alkenes, with appropriate counterions being potassium, sodium, aluminum, titanium, etc.

The processes preferably employed are Friedel-Crafts alkylations with alkenes using catalytic amounts of p-toluenesulfonic acid or methanesulfonic acid; or aluminum phenoxide additions across unactivated alkenes using catalytic amounts of diisobutyl-aluminum hydride or aluminum isopropoxide.

The process most preferably employed is the aluminum phenoxide addition of the resorcinol-tris-aryl-s-triazine across an unactivated alkene using catalytic aluminum isopropoxide, the reaction being run neat at temperatures between 110° and 250° C. The process is outlined below:

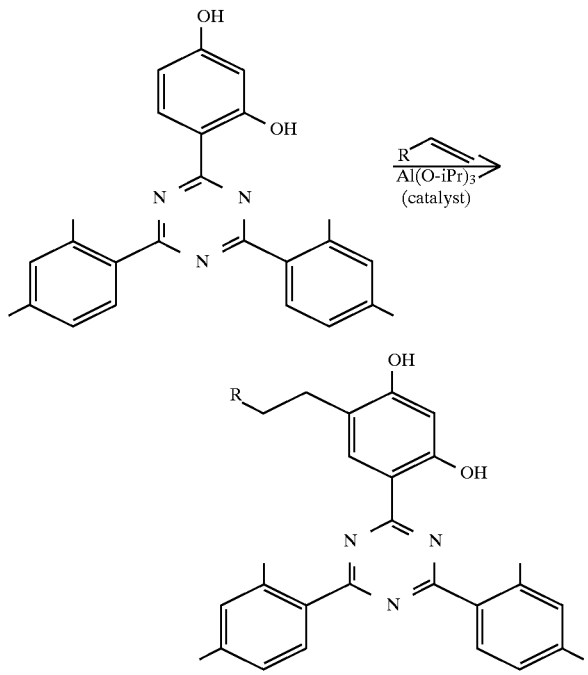

The process for making the instant compounds is preferably run with a two to ten excess equivalent amount of alkene, cycloalkene or phenylalkene compared to the amount of the compound of formula A

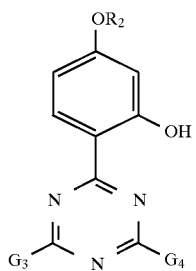

(A)

Still another aspect of the instant invention is a composition stabilized against the deleterious effects of actinic radiation which comprises (a) an organic material subject to degradation when exposed to actinic radiation, and (b) an effective stabilizing amount of a compound of formula I or II.

The organic material is preferably a polymer, especially a high solids thermoset acrylic/melamine resin or an acrylic urethane resin; most preferably a high solids thermoset acrylic/melamine resin.

Preferably, the composition is a polymer film compositions which comprises (a) an electro coat primer in adhesion to a metal substrate, (b) a base or color coat that is in adhesion to the electro coat and which comprises a film-forming binder and an organic pigment or an inorganic pigment or mixtures thereof, (c) a clear coat that is in adhesion to the base coat and which comprises a film-forming binder, and (d) an effective stabilizing amount, of at least one tris-aryl-s-triazine UV absorber contained in either the base coat or the clear coat or both base coat and clear coat.

The composition above contains as component (d) between 1 and 20% by weight of the film-forming binder.

Component (d) is preferably incorporated into the base coat.

The instant invention also pertains to the defined above which additionally contains an effective stabilizing amount of at least one 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-octylphenyl]-2H-benzotriazole;

2-{2-hydroxy-3-tert-butyl-5-[2-(omega-hydroxy-octa(ethyleneoxy)carbonyl)ethyl]-phenyl}-2H-benzotriazole; and 2-{2-hydroxy-3-tert-butyl-5-[2-(octyloxy)carbonyl)ethyl]phenyl}-2H-benzotriazole.

Preferably, the other tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine; and 2,4-bis(2,4-dimethylphenyl)-6-[2-hydroxy-4-(3-do-/tridecyloxy-2-hydroxy-propoxy)phenyl]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

To attain maximum light stabilization, the concurrent use of other conventional light stabilizers can be advantageous. Examples of such stabilizers are UV absorbers of the benzophenone, benzotriazole, s-triazine, cyanoacrylate or oxanilide type, or metal-containing light stabilizers, for example, organic nickel compounds, or hindered amine light stabilizers. In two-coat systems, these additional light stabilizers can be added to the clear coat or both in the clear coat and in the pigments base coat.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(α-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/ butadiene/styrene, /isoprene/styrene, /ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such a s epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed from about 1 to about 20% by weight of the stabilized composition, although this will vary with the particular substrate and application. An advantageous range is from 1 to 5%; preferably 1.5 to 2.5%.

The resulting stabilized compositions of the instant invention may optionally also contain from about 0.01 to about 5%, preferably from about 0.025 to about 2%, and especially from about 0.1 to about 1% by weight of various conventional additives, such as the materials listed below, or mixtures thereof.

Other compositions of special interest include those which additionally contain a UV absorber selected from the group consisting of the benzophenones, benzotriazoles, cyanoacrylic acid derivatives, hydroxyaryl-s-triazines, organic nickel compounds and oxanilides.

Preferred UV absorbers are selected from the group consisting of 2-[2-hydroxy-3,5-di-(α,α-dimethylbenzyl)phenyl]-2H-benzotriazole, 2-[2-hydroxy-3-(α,α-dimethylbenzyl)-5octylphenyl]-2H-benzotriazole, 2-(2-hydroxy-3,5-di-tert-amylphenyl)-2H-benzotriazole, 2-[2-hydroxy-3-tert-butyl-5-(ω-hydroxy-octa(ethyleneoxy)carbonyl)ethylphenyl]-2H-benzotriazole, 2-[2-hydroxy-3-tert-butyl-5-(2-octyloxycarbonylethyl)phenyl]-2H-benzotriazole, 4,4'-dioctyl-oxyoxanilide, 2,2'-dioctyloxy-5,5'-di-tert-butyloxanilide, 2,2'-didodecyloxy-5,5'-di-tert-butyloxanilide, 2-ethoxy-2'ethyloxanilide, 2,6-bis(2,4-dimethylphenyl)-4-(2-hydroxy-4-octyloxyphenyl-s-triazine, 2,6bis(2,4-dimethylphenyl)-4-(2,4-dihydroxyphenyl)-s-triazine, 2,4-bis(2,4-dihydroxyphenyl)-6-(4-chlorophenyl)-s-triazine, 2,6-bis(2,4-dimethylphenyl)-4-[2-hydroxy-4-(2-hydroxy-3-dodecyloxypropanoxy)-phenyl]-s-triazine and 2,2'-dihydroxy-4,4'-dimethoxybenzophenone.

Additional compositions of interest include those which additionally contain an effective stabilizing amount of a phenolic antioxidant; those which additionally contain a hindered amine derivative; or which additionally contain a phosphite or phosphonite stabilizer.

Compositions of special interest also include those wherein the organic material is an enamel of high solids content used for an industrial finish; is used as a coil coating; is used as a penetrating wood finish or is used as a film-forming wood finish.

When the instant compounds also contain a reactive functional group, said compounds can be chemically bonded by either condensation or free radical addition reaction to the polymer substrate. This provides for a non-migrating, non-sublimable UV absorber stabilizer. Such reactive functional groups include hydroxy, amino, amido, carboxyl and ethylenically unsaturated moieties.

The various organic materials useful in the instant invention are described in detail later in this application as well as are the various coadditives whose concomitant use with the instant compounds is often found to be highly beneficial.

The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example, 2,6di-tert-butyl-4-methylphenol
2-tert-butyl-4,6-dimethylphenol
2,5-di-tert-butyl-4-ethylphenol
2,6-di-tert-butyl-4-n-butylphenol
2,2-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example, 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example, 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-di-methoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetra-methylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tertbutyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilo-triacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine;
2,6-bis-(2,4-dimethylphenyl)-4-(2,4-dihydroxyphenyl)-s-triazine;
2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine;
2,4-bis[2-hydroxy4-(2-hydroxyethoxy)phenyl]-6-(4-bromophenyl)-s-triazine;
2,4-bis[2-hydroxy4-(2-acetoxyethoxy)phenyl]-6-(4-chlorophenyl)-s-triazine,
2,4-bis(2,4-hydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)penta-erythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3, 5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butyl-phenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-i-tert-butyl-4-hydroxybenzylmercaptoacetate, bis(3,5-di-tert-butyl-4-hydroxyhydrocinnamoyl)-hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6di-tert-butyl-p-cresol or 2,2'-ethylidene-bis-(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-1-3-oxopiperazin-4-yl)ethane, 2,2,4,4-tetramethyl-7-oxa-3,20 -diaza-21-oxodispiro[5.1.11.2] heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2, 6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N",N'''-tetrakis[(4,6-bis(butyl-2,2,6,6-tetramethyl-piperidin-4-yl)-amino-s-triazin-2-yl]-1, 10-diamino-4,7-diaza decane, mixed [2,2,6,6-tetramethylpiperidin-4-yl/β,β,β',β'-tetramethyl-3,9-(2,4,8, 10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8, 10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis( 2,2,6, 6-tetramethylpiperazinone-3-one), N-2,2,6, 6tetramethylpiperidin-4-yl-n-dodecylsuccinimide, N-1,2,2, 6,6-pentamethylpiperidin-4yl-n-dodecylsuccinimide, N-1-acetyl-2,2,6,6-tetramethylpiperidin-4-yl n-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-( 1-cyclohexyloxy-2,2,6,6-tetramethylpiperidin-4-yl) imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6, 6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octyl-amino-s-triazine and 4,4'-hexamethylenebis(amino-2,2,6,6-tetramethylpiperidine), N,N',N",N'''-tetrakis[(4,6-bis(butyl-(2,2,6,6-tetramethyl-piperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2, 2,6,6-tetramethylpiperidin-4-yl) succinate, 1-octyloxy-2,2, 6,6-tetramethyl-4-hydroxy-piperidine, poly-{[6-tert-octylamino-s-triazin-2,4diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are for illustrative purposes only and are not to be construed to limit the scope of the instant invention in any manner whatsoever.

EXAMPLE 1

1,3-Bis{1-[2,4-dihydroxy-5-(3,5-di(biphenylyl)-s-triazinyl))phenyl]-1-methyl-ethyl}benzene To a 500 mL three-necked, round-bottomed flask equipped with a magnetic stirrer, condenser, thermometer and a nitrogen atmosphere are charged 2-(2,4-dihydroxyphenyl)-4,6-di(biphenylyl)-s-triazine and a catalytic amount of aluminum isopropoxide. The mixture is heated to 185° C. and 1,3-diisopropenylbenzene is added all at once. The temperature is lowered to 132° C. and the mixture is stirred for six hours. After cooling to room temperature, the mixture is diluted with ethyl acetate, washed twice with water and once with brine. The organic layer is dried over anhydrous magnesium sulfate and filtered. The organic solvent is removed under reduced pressure. The crude product is purified with medium pressure chromatography using 12% ethyl acetate/heptane to afford the title compound.

EXAMPLE 2

Mixture of Methylene-Bis-2-(2-hydroxy-4-octyloxyphenyl)-4,6-di(biphenylylphenyl)-s-triazine; bridged in the 3:5, 5:5 and 3:3 positions in a 5:4:1 ratio To a 250 mL round-bottomed flask equipped with a condenser, magnetic stirrer and a nitrogen atmosphere are charged 2-(2-hydroxy4-octyloxyphenyl)-4,6-di (biphenylylphenyl)-s-triazine, diethoxymethane, a catalytic amount of p-toluenesulfonic acid and dioxane. The mixture is stirred at 90° C. for 28 hours, and is then allowed to cool to room temperature and diluted with a portion of ethyl acetate. The mixture is washed three times with water, three times with saturated sodium bicarbonate solution and then with brine. The organic layer is dried over anhydrous magnesium sulfate and filtered. The organic solvent is removed under reduced pressure to afford of a glass. The crude product is purified with medium pressure chromatography with 19:1 heptane:ethyl acetate to afford the methylene bridged dimer mixture as a glassy solid.

This mixture conforms to formula I where t is 0. There are also small to trace amounts of higher "oligomers" where t is 1, 2 and/or 3 seen in the spectral analyses of this mixed isomer product.

EXAMPLE 3

Mixture of Benzylidene-bis-2-(2-hydroxy-4-octyloxyphenyl)-4,6-di(biphenylyl)-s-triazine; bridged in the 3:5 and 5:5 positions in a 1:1 ratio To a 250 mL round-bottomed flask equipped with a condenser, magnetic stirrer and a nitrogen atmosphere are charged 2-(2-hydroxy-4-octyloxy phenyl)-4,6-di (biphenylyl)-)s-triazine, benzaldehyde and a catalytic amount of p-toluenesulfonic acid. The mixture is stirred at 140° C. for three hours, and is then allowed to cool to room temperature. The mixture is taken up in ethyl acetate and is washed twice with saturated sodium bicarbonate, once with water and then with brine. The organic layer is dried over anhydrous magnesium sulfate and filtered. The organic solvent and excess benzaldehyde are removed under reduced pressure to afford a crude product which is then purified with medium pressure chromatography with 19:1 heptane:ethyl acetate to afford the benzylidene bridged dimer mixture.

This mixture conforms to formula I where t is 0 and L is benzylidene.

EXAMPLE 4

Delamination Resistance of High Solids Thermoset Acrylic Clear Coats Containing UV Absorbers Applied over UV Transparent Base Coats Test panels are prepared by spray applying a 1.8–2.0 mil (0.036–0.051 mm) thick film of a commercially available high solids thermoset acrylic melamine clear coat, containing 2% by weight, based on the acrylic melamine resin, of a test UV absorber stabilizer of this invention, over a commercially available UV transparent base coat, wet-on-wet. The topcoat is applied over 4"×12" (10.16 cm×30.48 cm) UNIPRIME® panels obtained from Advance Coatings Technology, Inc. The coated panels are then baked at 250° F. (121° C.) for 30 minutes. After storage for one week in an air-conditioned room, the panels are exposed in Florida at 5° South, black box according to SAE J-1976. The panels are exposed for one year. After one year, a humidity test is conducted consisting of exposing the panels to 100° F. (38° C.) and 100% humidity for four days. After four days, a tape adhesion test is performed.

The instant compounds are effective in improving adhesion of the clear coat to the base coat during weathering.

EXAMPLE 5

Delamination Resistance of Acrylic Urethane Clear Coats Containing UV Absorbers Applied Directly over Electrocoat Primer Test panels are prepared by spray applying a 1.8–2.0 mil (0.036–0.051 mm) thick film of a commercially available acrylic urethane clear coat, containing 2% by weight, based on the acrylic urethane resin, of a test UV absorber stabilizer of this invention, directly over 4"×12" (10.16 cm×30.48 cm) UNIPRIME® panels obtained from Advance Coatings Technology, Inc. The coated panels are then baked at 250° F. (121° C.) for 30 minutes. After storage for one week in an air-conditioned room, the panels are exposed in Florida at 5° South, black box according to SAE J-1976. The panels are evaluated every day for delamination and are retired from the test when delamination is evident over 10% of the panel area.

The instant compounds are effective in delaying delamination of the clear coat from the electrocoat primer.

EXAMPLE 6

The following example demonstrates the utility of the o-hydroxyphenyl-s-triazines of the instant invention in a laminated polycarbonate plaque wherein the UV absorber is incorporated only into the thin surface protecting layer such as prepared in a coextruded article.

Laminated plaques are prepared by bonding a 1 mil (0.0254 mm) polycarbonate film (LEXAN® 141-111N), General Electric Co.) containing 5% by weight of an UV absorber to a non-UV stabilized 125 mil (3.18 mm) polycarbonate plaque (LEXAN® 141-111N) via compression molding in a Wabash Compression molder at 350° F. (177° C.) for three minutes at 1000 psi (70 Kg/cm$^2$), three minutes at 3000 psi (210 Kg/cm$^2$), and then three minutes at 3000 psi (210 Kg/cm$^2$) while cooling. The plaques are then exposed in an Atlas CI-65 Xenon Arc Weatherometer, using the ASTM designation G26-88 Test Method C with the protective layer facing the incident light. Polymer degradation is determined by measuring yellowness index (YI) on an ACS spectrophotometer.

The o-hydroxyphenyl-s-triazines of the instant invention are very effective in protecting the polycarbonate sheet from degradation and discoloration.

EXAMPLE 7

Polypropylene fiber samples are prepared by extruding fiber grade polypropylene containing a pigment, a phosphite, a phenolic antioxidant or hydroxylamine, a metal stearate, a UV absorber or hindered amine light stabilizer or a combination of a UV absorber and hindered amine light stabilizer.

The pigment is added as a pigment concentrate which is prepared from pure pigment and polypropylene resin (PROFAX® 6301, Himont) by mixing the two components in a high shear mixer in a ratio of 25% pigment and 75% resin, pressing the resulting resin/pigment mixture on a Wabash Compression Molder (Model # 30-1515-4T3) into a thin sheet and then dividing the sheet into fine chips for dispersion in fresh polypropylene resin at reduced concentrations.

All additive and pigment concentrations in the final formulations are expressed as weight percent based on the resin.

The formulations contain 0.05–0.1% phosphite, 0–1.25% phenolic antioxidant, 0–0.1% hydroxylamine, 0.05–0.1% calcium stearate, 0–1.25% UV absorber of this invention and/or 0–1.25% hindered amine stabilizer. The materials are dry-blended in a tumble dryer, extruded on a Superior/MPM 1" (2.54 cm) single screw extruder with a general all-purpose screw (24:1 L/D) at 475° F. (246° C.), cooled in a water bath and pelletized. The resulting pellets are spun into fiber at about 525° F. (274° C.) on a HILLS Research Fiber Extruder (Model # REM-3P-24) fitted with a 41 hole, delta configuration spinnerette. The spun tow is stretched at a draw ratio of 3.2:1 producing a final denier of 615/41.

The fiber samples are knitted into socks on a Lawson-Hemphill Fiber Analysis Knitter, cut into appropriate lengths and exposed in an Atlas Ci65 Xenon Arc Weather-Ometer at 89° C. black panel temperature, 0.55 W/m² at 340 nanometers and 50% relative humidity (Society of Automotive Engineers SAE J 1885 Test Procedure).

Fiber samples are tested by performing color measurements on an Applied Color Systems spectrophotometer by reflectance mode according to ASTM D 2244-79 at regular intervals. Identical, but separate, samples are examined for catastrophic failure.

While the UV absorbers of this invention do not adequately protect the pigmented polypropylene fiber from actinic induced degradation when used in the absence of a hindered amine, the combination of a UV absorber of this invention with a hindered amine provides far superior protection to the pigmented polypropylene fiber, indeed synergistic stabilization protection over the level of protection provided by the hindered amine alone when used at the same total concentration.

The same superior stabilization is seen when the pigmented polypropylene fiber is replaced with pigmented nylon or polyester fiber.

What is claimed is:

1. A composition stabilized against the deleterious effects of actinic radiation which comprises
    (a) a polymer subject to degradation when exposed to actinic radiation, and
    (b) an effective stabilizing amount of a compound of formula I

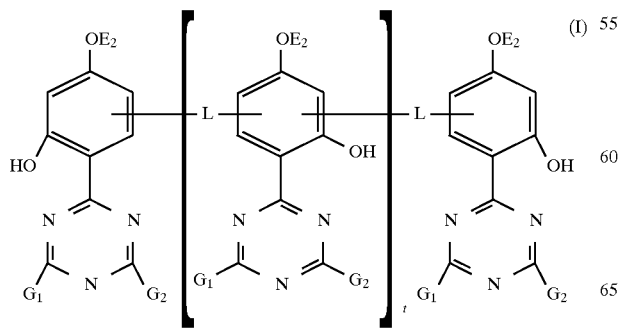

wherein $G_1$ is a group of the formula

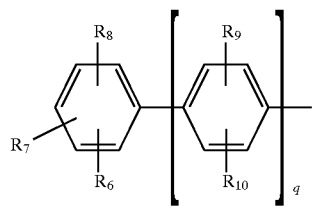

$G_2$ is a group of the formula

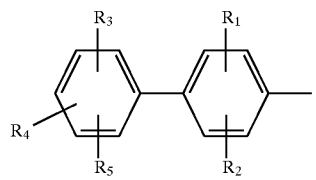

where q is 0 or 1, $R_1$, $R_2$, $R_3$, $R_4$, $R_5$, $R_6$, $R_7$, $R_8$, $R_9$ and $R_{10}$ are independently of one another hydrogen, hydroxyl, cyano, alkyl of 1 to 20 carbon atoms, alkoxy of 1 to 20 carbon atoms, phenylalkyl of 7 to 15 carbon atoms, cycloalkyl of 4 to 12 carbon atoms, cycloalkoxy of 4 to 12 carbon atoms, halogen, haloalkyl of one to 5 carbon atoms, sulfonyl, carboxyl, acylamino of 2 to 12 carbon atoms, acyloxy of 2 to 12 carbon atoms, alkoxycarbonyl of 2 to 12 carbon atoms, aminocarbonyl, or $R_3$ and $R_4$ together with the phenyl radical to which they are attached, are a cyclic radical interrupted by one or more oxygen or nitrogen atoms, $E_2$ is hydrogen, straight or branched chain alkyl of 1 to 24 carbon atoms or cycloalkyl of 5 to 12 carbon atoms; or said alkyl or cycloalkyl substituted by one to eight halogen, epoxy, glycidyloxy, furyloxy, —$E_4$, —$OE_5$, —$N(E_5)_2$, —$CON(E_5)_2$, —$COE_5$, —$COOE_5$, —$OCOE_5$, —$OCOC(E_5)=C(E_5)_2$, —$C(E_5)=CCOOE_5$, —CN, —NCO, or

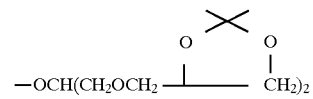

combination thereof; or said alkyl or cycloakyl interrupted by one to six epoxy, —O—, —$NE_5$—, —$CONE_5$—, —COO—, —OCO—, —CO—, —$C(E_5)=C(E_5)COO$—, —$OCOC(E_5)=C(E_5)$—, —$(E_5)C=C(E_5)$—, phenylene, or -phenylene-$G_3$-phenylene in which $G_3$ is —O—, —S—, —$SO_2$—, —$CH_2$—, or —$C(CH_3)_2$—, or combinations thereof; or said alkyl or cycloalkyl both substituted and interrupted by combinations of the groups mentioned above; or $E_2$ is —$SO_2E_3$, or —$COE_6$;

$E_4$ is aryl of 6 to 10 carbon atoms, or said aryl substituted by one to three halogen alkyl of 1 to 8 carbon atoms, or combinations thereof; cycloalkyl of 5 to 12 carbon atoms; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combination thereof; or straight or branched chain alkenyl of 2 to 18 carbon atoms;

$E_5$ is defined as $E_4$, or $E_5$ is also hydrogen or straight or branched chain alkyl of 1 to 24 carbon atoms or $E_5$ is a group of the formula

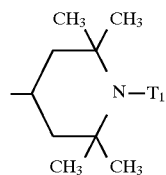

where $T_1$ is hydrogen, oxyl, hydroxyl, alkyl of 1 to 12 carbon atoms, said alkyl substituted by at least one hydroxyl or lower alkoxy, benzyl or alkanoyl of 2 to 18 carbon atoms, $E_6$ is straight or branched chain alkyl of 1 to 18 carbon atoms, straight or branched chain alkenyl of 2 to 18 carbon atoms, phenyl, alkoxy of 1 to 12 carbon atoms, phenoxy, alkylamino of 1 to 12 carbon atoms, arylamino of 6 to 12 carbon atoms or a group —$E_7$COOH or —NH—$E_8$—NCO;

$E_7$ is alkylene of 2 to 14 carbon atoms or o-phenylene;

$E_8$ is alkylene of 2 to 10 carbon atoms, phenylene, tolylene, diphenylenemethane or a group

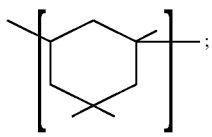

t is 0 to 9; and

L is straight or branched chain alkylene of 1 to 12 carbon atoms, cycloalkylene of 5 to 12 carbon atoms, alkylene by or interrupted by cyclohexylene or phenylene; or L is benzylidene; or L is —S—, —S—S—, —S—$L_1$—S—, —SO—, —SO$_2$—, —SO—$L_1$—SO—, —SO$_2$—$L_1$—SO$_2$—, —CH$_2$—NH—$L_1$—NH—CH$_2$— or

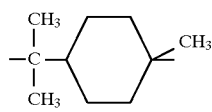

where $L_1$ is alkylene of 2 to 12 carbon atoms, cycloalkylene of 5 to 12 carbon atoms, or alkylene interrupted or terminated by cyclohexylene of 8 to 12 carbon atoms; with the proviso that at least one L linkage is attached to the phenyl ring in the 5-position.

2. A composition according to claim 1 where in formula I, $G_1$ and $G_2$ are biphenyl substituted with one to three lower alkyl or halogen;

$E_2$ is straight or branched chain alkyl of 2 to 24 carbon atoms, or said alkyl substituted by one or two —OE$_5$, where $E_5$ is hydrogen, straight or branched chain alkyl of 1 to 24 carbon atoms, or phenyl.

3. A composition according to claim 2 where in formula I, $E_2$ is alkyl of 2 to 24 carbon atoms substituted by one hydroxyl and by one —OE$_5$ where $E_5$ is alkyl of 1 to 24 carbon atoms or phenyl.

4. A composition according to claim 1 where in formula I, $G_1$ and $G_2$ are biphenylyl substituted with one to three lower alkyl or halogen;

t is 0 to 3; and

L is methylene; benzylidene;

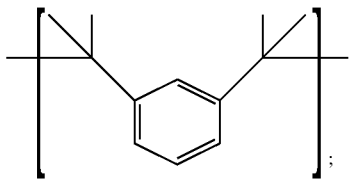

or

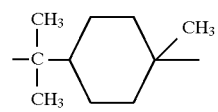

5. A composition according to claim 1 where in formula I, $G_1$ and $G_2$ are 4-biphenylyl;

$E_2$ is straight or branched chain alkyl of 2 to 6 carbon atoms, or said alkyl substituted by one or two —OE$_5$ where $E_5$ is hydrogen or straight or branched chain alkyl of 1 to 24 carbon atoms.

6. A composition according to claim 5 where in formula I, $E_2$ is alkyl of 1 to 24 carbon atoms substituted by one hydroxyl and by one alkoxy of 1 to 24 carbon atoms.

7. A composition according to claim 1 wherein the compound of formula I is a. 1,3-bis{1-[2,4-dihydroxy-5-(3,5-di(4-biphenylyl)-s-triazinyl))phenyl]-1-methyl-ethyl}benzene;

b. mixture of methylene-bis-[2-(2-hydroxy-4-octyloxyphenyl)-4,6-di(4-biphenylyl)-s-triazine bridged in the 3:5, 5:5 and 3:3 position in a 5:4:1 ratio; and c. mixture of benzylidene-bis-[2-(2-hydroxy-4-octyloxyphenyl)-4,6-di(4-biphenylyl)-s-triazine]; bridged in the 3:5 and 5:5 position in a 1:1 ratio.

8. A composition according to claim 7 wherein the compound of formula I is b. mixture of methylene-bis-2-(2-hydroxy-4-octyloxyphenyl)-4,6-di(4-biphenylyl)-s-triazine; bridged in the 3:5, 5:5 and 3:3 position in a 5:4:1 ratio.

9. A composition according to claim 1 wherein the polymer is a high solids thermoset acrylic/melamine resin or an acrylic urethane resin.

10. A composition according to claim 9 wherein the polymer is a high solids thermoset acrylic/melamine resin.

11. A composition according to claim 1 where the composition is a polymer film composition which comprises (a) an electro coat primer in adhesion to a metal substrate, (b) a base or color coat that is in adhesion to the electro coat and which comprises a film-forming binder and an organic pigment or an inorganic pigment or mixtures thereof, (c) a clear coat that is in adhesion to the base coat and which comprises a film-forming binder, and (d) an effective stabilizing amount, of at least one tris-aryl-s-triazine UV absorber contained in either the base coat or the clear coat or both base coat and clear coat.

12. A composition according to claim 11 wherein component (d) is between 1 and 20% by weight of the film-forming binder.

13. A composition according to claim 11 wherein component (d) is incorporated into the base coat.

14. A composition according to claim 11 which additionally contains an effective stabilizing amount of at least one 2-hydroxyphenyl-2H-benzotriazole; another tris-aryl-s-triazine; or hindered amine light stabilizer or mixtures thereof.

15. A composition according to claim 14 wherein the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-octylphenyl]-2H-benzotriazole;

2-{2-hydroxy-3-tert-butyl-5-[2-(omega-hydroxy-octa(ethyleneoxy)carbonyl)ethyl]-phenyl}-2H-benzotriazole; and 2-{2-hydroxy-3-tert-butyl-5-[2-(octyloxy)carbonyl)ethyl]phenyl}-2H-benzotriazole.

16. A composition according to claim 14 wherein the other tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine; and 2,4-bis(2,4-dimethylphenyl)-6-[2-hydroxy-4-(3-do-/tridecyloxy-2-hydroxy-propoxy)phenyl]-s-triazine.

17. A composition according to claim 14 which contains an effective amount of hindered amine light stabilizer.

18. A composition according to claim 17 wherein the hindered amine is selected from the group consisting of bis(2,2,6,6-tetramethylpiperidin-4-yl) sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N",N'"-tetrakis[(4,6-bis(butyl-2,2,6,6-tetramethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane)diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl] 1,2,3,4-butanetetracarboxylate, octamethylene bis(2,2,6,6-tetramethylpiperidin4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yl n-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

19. A composition according to claim 17 wherein the hindered amine is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxy-piperidine and succinic acid, the polycondensation product of 2,4-dichloro-6-tert-octylamino-s-triazine and 4,4'-hexamethylenebis(amino-2,2,6,6-tetramethylpiperidine), N,N',N",N'"-tetrakis[(4,6-bis(butyl-(2,2,6,6-tetramethylpiperidin-4-yl)amino)-s-triazine-2-yl]-1,10-diamino-4,7-diazadecane, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

20. A composition according to claim 11 wherein the film-forming binder is a high solids thermoset acrylic/melamine resin.

21. A composition according to claim 11 wherein the film-forming binder is an acrylic urethane resin.

* * * * *